United States Patent [19]
Phillips et al.

[11] Patent Number: 5,261,918
[45] Date of Patent: Nov. 16, 1993

[54] SHEATHED SURGICAL INSTRUMENT AND APPLICATOR KIT

[75] Inventors: John C. Phillips, Holly springs; Richard M. Malec, Durham, both of N.C.

[73] Assignee: Edward Weck Incorporated, Princeton, N.J.

[21] Appl. No.: 874,502

[22] Filed: Apr. 27, 1992

[51] Int. Cl.5 .............................. A61B 17/00
[52] U.S. Cl. ........................ 606/140; 606/1; 606/41; 606/51; 606/52; 606/205
[58] Field of Search .......... 606/41, 51, 52, 45, 606/46, 47, 48, 49, 50, 139, 140, 141, 205, 207

[56] References Cited

U.S. PATENT DOCUMENTS

| | | | |
|---|---|---|---|
| 617,247 | 1/1899 | Gholson | 606/205 |
| 1,714,220 | 5/1929 | Groff | 606/51 |
| 2,704,061 | 3/1955 | Amspacker | 606/140 |
| 3,840,003 | 10/1974 | Komiya | 606/207 |
| 4,122,856 | 10/1978 | Mosior et al. | 606/170 |
| 4,416,275 | 11/1983 | Omley | 606/140 |
| 4,817,630 | 4/1989 | Schintgen et al. | 128/772 |
| 5,014,407 | 5/1991 | Boughten et al. | 606/207 |

Primary Examiner—Stephen C. Pellegrino
Assistant Examiner—Jeffrey A. Schmidt
Attorney, Agent, or Firm—Rosenblatt & Associates

[57] ABSTRACT

A kit for protectively sheathing the proximally unenclosed portion of a grasping members pair of a surgical instrument assembly resulting from the sheathing is disclosed, the kit including an applicator for spreading the lumen of an elastic tubular sheath member which is mounted on the surgical instrument over unenclosed portions of the grasping jaws adjacent to the distal body mounting the grasping jaws, the sheath member and body member preferably being formed of dielectric material for electrocauterization.

34 Claims, 5 Drawing Sheets

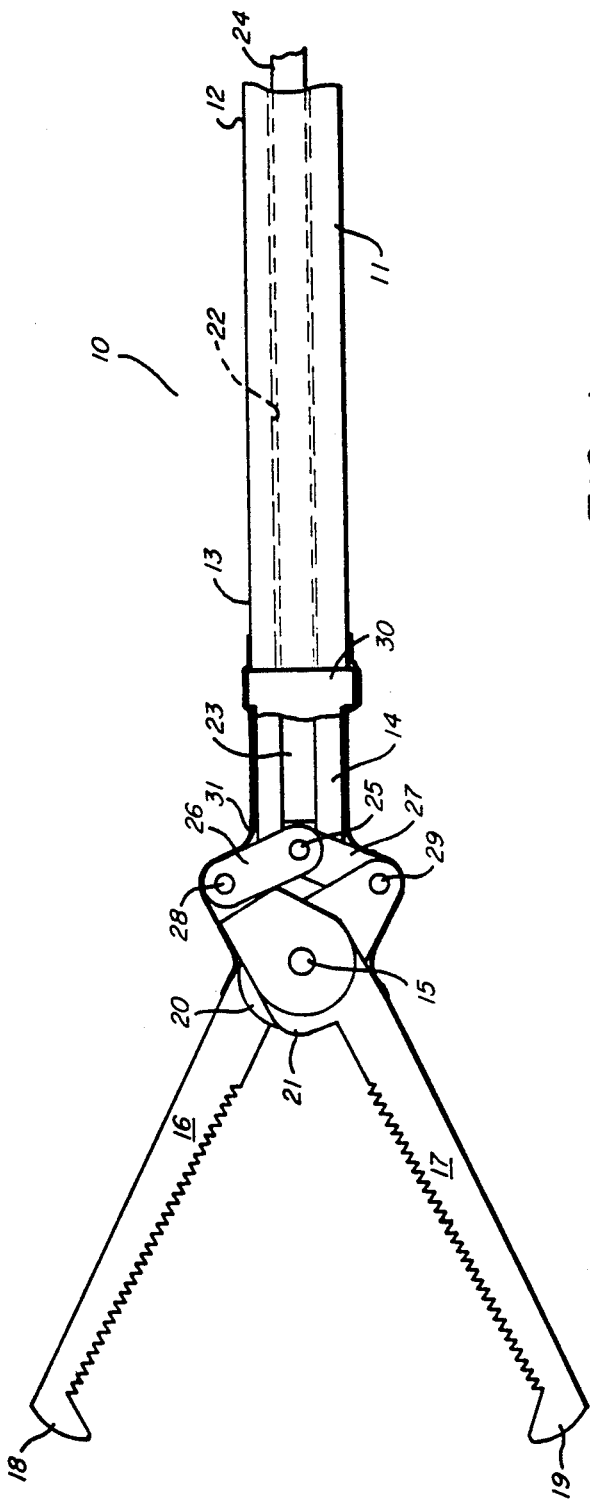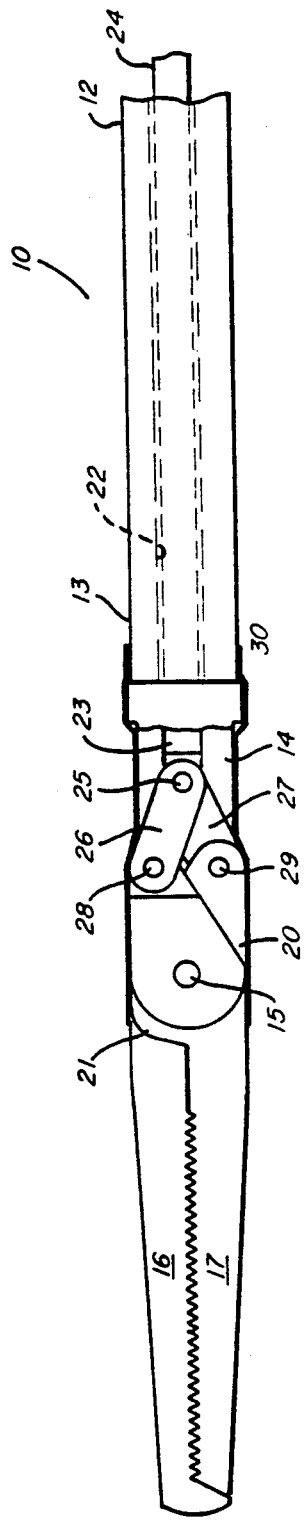
FIG. 1
FIG. 2

SHEATHED SURGICAL INSTRUMENT AND APPLICATOR KIT

FIELD OF THE INVENTION

This invention relates to surgical instruments which are inserted into body cavities and manipulated to grasp and slice or tear samples of tissue from the body anatomy and, more particularly, relates to such instruments in which the tips of the instruments are employed to electrocauterize the wound resulting from the surgical maneuver.

BACKGROUND OF THE INVENTION

Surgical instruments are known in the prior art that are inserted into body cavities, such as urethras, rectum, vagina and uterus, throat, etc., to grip, tear or slice tissue samples from the particular anatomy of interest. These instruments have a jaw portion at a distal end. The jaws, or one of them, moves about a hinge and are activated by a rod reciprocating in a tubular body or other support. Often, tissue becomes entrapped in the hinge area and can cause several problems. When entrapped in the hinge area, the performance of the instrument can be adversely affected during the procedure. If the entrapped tissue is not simply loose tissue, the instrument can become lodged and must be pulled free, with resultant unintended wounding of the anatomy. Subsequent to the procedure, the instrument, which is intended to be durable and reusable, is meant to be cleaned and sterilized. Entrapped tissue becomes a major cleaning problem.

In addition, many of these instruments are electrocauterizing instruments which employ an electrical current to cauterize and staunch the flow of blood resulting from the insulted tissue affected by the maneuver. The body mounting the hinged jaws at its distal end is formed of a dielectric material in these electrosurgical instruments. A common complaint of such electrosurgical instruments is inadvertent electrical burns upon the anatomy of the patient. Such instruments are typically insulated with a dielectric material to within an inch or so of the distal portion of the device. The insulation does not extend farther because the jaws must be allowed to move freely and have to be cleaned and sterilized between procedures. However, with so much of the distal portion of the device exposed, it becomes more difficult for the surgeon to control the exact site of electrocoagulation, creating a risk of inadvertent patient burns since electrical current follows the path of least resistance, which may not necessarily be through the cauterizing tip of the instrument.

The use of sleeves at the tips of electrosurgical devices is illustrated in U.S. Pat. Nos. 4,834,095; 4,719,914; 4,076,028; and 3,920,021. These sleeves are permanently fixed to the instrument and do not require radial flexibility to serve their intended purpose. Spreader devices for various applications are illustrated in U.S. Pat. Nos. 2,447,474; 4,370,979; 4,921,423; and 509,226.

Accordingly, it is an object of this invention to provide a sheath for a surgical instrument in which a distal portion which radially expands is covered during the surgical manipulation to prevent entrapment of tissue.

It further is an object of this invention to provide an electrosurgical instrument in which the risk of inadvertent patient burn is reduced.

SUMMARY OF THE INVENTION

These and other objects of the invention are attained through provision of a kit for protectively sheathing the proximally unenclosed portion of a grasping members pair of a surgical instrument and by provision of the assembled surgical instrument so protectively sheathed. The unprotected surgical instrument intended to be protectively sheathed comprises an elongated tubular body having a lumen through it. The body mounts a grasping members pair, or jaws, at the distal end of the body. The grasping members pair are manipulatable through a normal opening and closing range of motion by a means for actuating the jaws received within the lumen. The grasping members pair, or jaws, include a distal tip portion and a portion remotely proximal of the tip portion at least partially unenclosed by the body. The grasping members pair are mounted to the body in a proximal portion of the grasping members pair. The kit includes an elastic tubular sheath member (i) of length sufficient to cover the remotely proximal portion of the grasping members pair and bridge to an adjacent distal portion of the tubular body, (ii) having a sheath lumen of perimeter not greater than the perimeter of the adjacent distal portion of the body, effective, for the elasticity of such sheath member to fit so tensioned when installed in a bridging position covering the remotely proximal portion of the grasping members pair, and bridging to the adjacent distal portion of such body, as to remain longitudinally in place when the grasping members pair is actuated through its normal range of motion, and (iii) of elasticity to allow full range of movement of the grasping members pair upon actuation of them when the sheath member is installed in the bridging position.

The kit further includes an applicator for applying the sheath member to the remotely proximal portion of the grasping members pair. The applicator includes first and second elongated finger members, each having proximal and distal segments, and including between such segments a pair of hinge pin stands supporting a hinge pin off the finger member transversely to the finger member length. The finger members are opposedly connected side-by-side adjacent to each other by means of a hinge pin and each pair of the hinge pin stands. The distal segments of the finger members include distal extremity portions having dimensions allowing them to be insertable into the lumen of the sheath member for substantially the length of the lumen. The hinge pin stands are spaced from the distal end of the distal segment extremities portions at least the distance between the distal tip of the grasping members pair and the adjacent distal portion of the body of the surgical instrument. At least one of the first and second finger members diverges proximally from the distal extremity portion of it to space it apart from the other finger member at the hinge pin stand connection, sufficiently for the tip of the grasping members pair to be received between the finger members at least until the adjacent distal portion of the tubular body is between the distal extremity portions of the fingers, at the time when at least one of the proximal segments of the finger members is pivoted on a hinge pin toward the other proximal segment, thereby moving the distal portions of the fingers away from each other.

The kit may further also include a cartridge for holding the sheath members for pickup by the applicator.

The sheath member is preferably a dielectric. A surgical grasping instrument, assembled with a removable elastic tubular sheath member in accordance with this invention and preferably a dielectric sheath member, accomplishes the goals of this invention to prevent entrapment of tissue in a hinge area in of the grasping device and, in the dielectric embodiment of the sheath, reduces the risk of inadvertent patient burn when the grasping device is an electrosurgical instrument.

BRIEF DESCRIPTION OF THE DRAWINGS

FIG. 1 is a side elevational view of a surgical grasping instrument assembly and partial longitudinal section, showing a grasping members pair in an open position.

FIG. 2 is the same view as FIG. 1, showing the instrument assembly with the grasping members pair in closed position.

DETAILED DESCRIPTION OF THE PREFERRED EMBODIMENT

Figure 3:
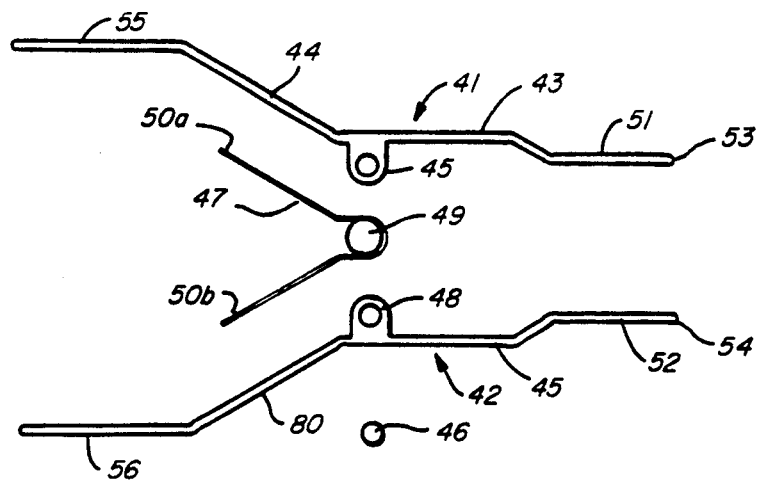
FIG. 3 is an exploded side elevational view of an applicator for applying a sheath for the surgical grasping instrument assembly shown in FIG. 1.

Referring now to the drawings, the invention is described in reference to a preferred embodiment. It will be understood that the invention itself is not restricted to the particular form disclosed in the preferred embodiment, but is described by the claims following the description of the invention.

Referring first to FIG. 1, a surgical grasping instrument assembly is referred to generally by reference numeral 10. The scope of the invention is broader than grasping instruments as such. It encompasses other instruments that perform other functions where movement of parts or use of the instrument may present places for tissue to be trapped. It further comprises the use of disposable sheaths that can remain in place longitudinally during a procedure even under significant radial or outward deflections. It also encompasses instruments that need insulation to prevent cauterizing at an improper location and the sheath and its applicator allowing the use of disposable sheaths to facilitate sterilization for reuse. The instrument assembly includes an elongated inelastic tubular body 11, having a proximal segment 12 at the opposite end of a distal segment 13. The proximal segment is broken away and its full extent is not shown. The distal segment 13 includes means for mounting a grasping members pair at the distal end of the distal body segment 13. The means for mounting a grasping members pair suitably include a clevis 14, one member of which is seen in the longitudinal partial segmental view of FIG. 1, and a hinge pin 15 interconnecting the two arms of the clevis. A grasping members pair includes jaw members 16, 17. Each jaw member has a tip portion 18, for upper jaw member 16, and 19 for jaw member 17, as well as a portion remotely proximal of the tip portion; for jaw member 16, the remotely proximal portion is indicated by reference numeral 20, and for jaw member 17, the remotely proximal portion is indicated by reference numeral 21. Jaw member 16 is mounted on pin 15 in the remotely proximal portion 20 of jaw member 16, and jaw member 17 is mounted on pin 15 in the remotely proximal portion 21 of jaw member 17.

Figure 10:
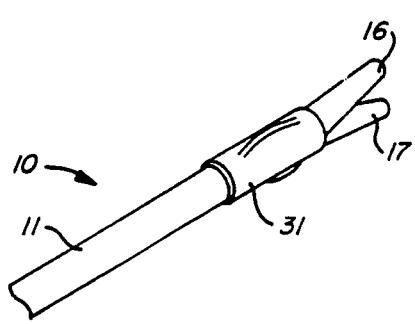
FIG. 10 shows the installation of the sheath member complete with the applicator withdrawn.

Tubular body member 11 defines a lumen 22 therethrough, indicated by a dashed line. Means are received within lumen 22 for connection to the grasping members pair 16, 17 for actuating the members pair remotely to move one or both of them through an opening and closing full range of movement. As illustrated, a rod member 23 having proximal portion 24 and distal portion 25 is reciprocatively received within lumen 22. The proximal rod portion 24 extends in part exteriorly of body member 22 for manipulation external to the body member 11. The distal portion 23 is connected to means co-active with jaw members 16, 17 to open and close such members. As illustrated, such means include a hinge pin 25 acting on links 26, 27 pivotally connected to, for link 27, the most proximal extremity of remotely proximal portion 20 of jaw 16, and for link 26, the most proximal extremity of remotely proximal portion 21 of jaw 17. Bridging both the remotely proximal portions 20, 21 of jaw members 16, 17, and the adjacent distal portion 30 of the distal segment of tubular body 11, is an elastic, tubular, preferably dielectric, sheath member 31. Sheath 31 is of length sufficient to cover the proximal portion 20, 21 of grasping members pair 16, 17 and bridge to an adjacent distal portion 30 of body 11. The lumen 70 (see FIG. 8) of sheath 31, in its undistended perimeter, has a perimeter not greater than the perimeter of the adjacent distal portion 30 of body 11, effective, for the elasticity of sheath member 31 to fit so tensioned when installed in a bridging position covering the proximal portion 20, 21 of the grasping members pair 16, 17 and bridging to the adjacent distal portion 30 of body 11, as to remain longitudinally in place when grasping members pair 16, 17 is actuated through its normal range of movement, as illustrated in FIGS. 1 and 10. Sheath member 31 is of such elasticity as to allow the normal range of movement of grasping members pair 16, 17 upon actuation, as by reciprocation of rod member 24, when sheath member 31 is installed in the bridging position.

Figure 11:
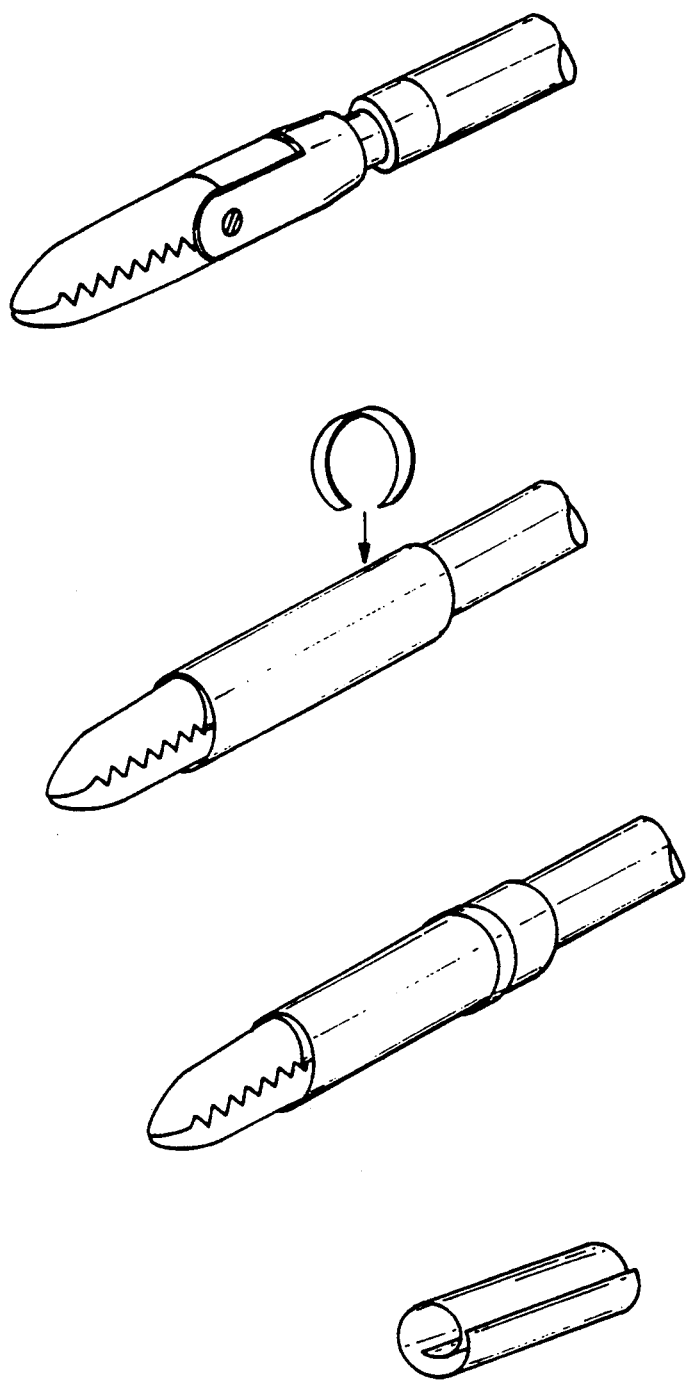
FIG. 11 shows a method of forming the sheath and applying it to an instrument.

Preferably, the body 11 and sheath 31 are a dielectric material and the surgical instrument 10 is useful for electrocauterization. To this end, electrical current may be conducted to the jaws 16, 17 by means well known in the art. Suitable dielectric materials useful for the body 11 include thermoplastic elastomers, polyurethanes, silicone rubber, latex rubber, or nitrile rubber. Preferably, the sheath 31 is formed of a polyurethane material having the following characteristics: high ultimate elongation (750%), excellent elastic recovery, good dielectric strength, and inherent lubricity (for ease of application). Such a material can be styrene-ethylene butylene-styrene block copolymer (SEBS). The sheath 31 can be tubular or it can be formed from sheet rolled around the instrument and secured with a snap ring retainer, elastic band, adhesive, or the like, to the instrument 10, as shown in FIG. 11.

Although illustrated as a grasping members pair, both members of which open and close, it is contemplated within the scope of this invention that one jaw member may be fixed and only the other jaw member pivotable to open and close for grasping.

Figure 4:
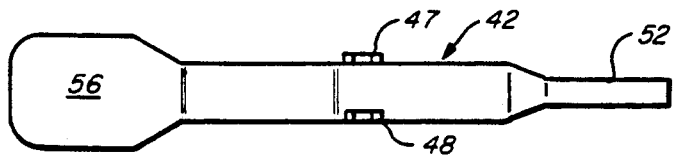
FIG. 4 is a plan view of the exploded applicator illustrated in FIG. 3.
Figure 4:
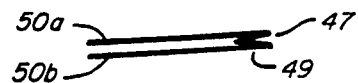
Figure 4:
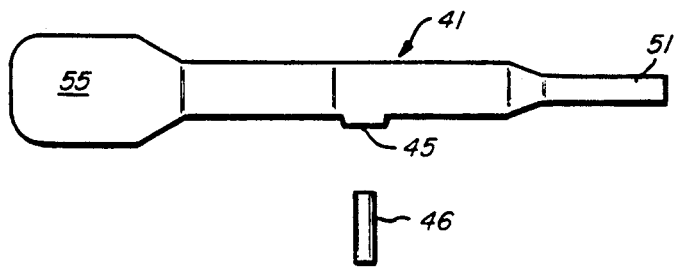
Figure 5:
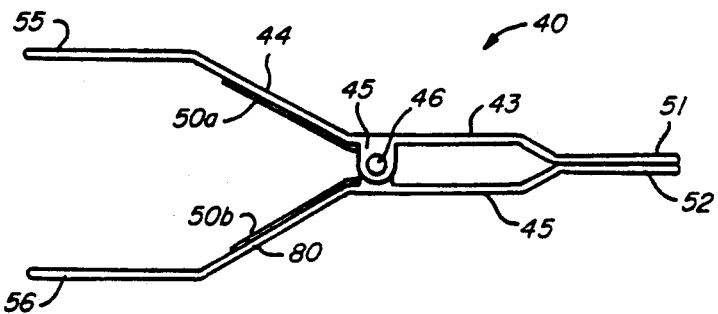
FIG. 5 is a combined side elevational view and plan view of the applicator in assembled form illustrated exploded in FIGS. 3 and 4.
Figure 5:
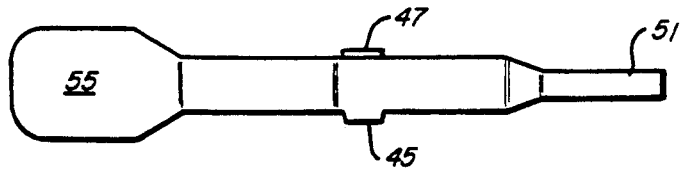

Referring now to FIGS. 3-5, an applicator, indicated generally by reference numeral 40, is illustrated. Applicator 40 is employed to apply sheath 31 to the remotely proximal portions 20, 21 of the grasping pair member 16, 17. Applicator 40 includes first and second elongated finger members 41, 42, each having a proximal segment and a distal segment. Finger member 41 has proximal segment 43 and distal segment 44. Finger member 42 has proximal segment 45 and distal segment 46. Finger member 41 has between proximal segment 43 and distal segment 44, a pair of hinge pin stands 45, 46. Finger member 42 has a pair of hinge pin stands 47, 48, best seen to advantage in FIG. 4. The hinge pin stands of each of fingers 41, 42 support a hinge pin 46 of the finger member transversely to the longitudinal direction of the finger member. A torsional spring 47 includes an eye 49, which receives hinge pin 46, with the legs 50a, 50b of the torsional spring being oriented in the direction of the proximal segments 44, 46 of fingers 41, 42, which are opposingly connected side-by-side adjacent to each other by hinge pin 46 in each of the pair of hinge pin supports 45, 46 and 47, 48 in members 41, 42, as seen in FIG. 5. The extremity portion 51 of distal segment 43 of finger member 41, and the extremity portion 52 of the distal segment 45 of member 42 each have a dimension, such that when approximated, as shown in FIG. 5, the extremities 51, 52 are insertable into the lumen of a sheath member 31. The hinge pin stands 45-48 are spaced from the ends 53, 54 of the distal extremity portions 51, 52, a length at least equal to the distance between the distal tips 18, 19 of the grasping members pair 16, 17, and the adjacent distal portion 30 of tubular body 11. Finger members 42, 43 each diverge proximally from their distal extremity portions 51, 52 to space finger members 41, 42 apart at the hinge pin stands connection as seen in FIG. 5. This divergence is sufficient to separate finger members 41, 42 at hinge pin stands 45-48 enough for tips 18, 19 of the grasping members pair 16, 17 to be advanced between finger members 41, 42, at least until the adjacent distal portion 30 of tubular body 11 is adjacently between the extremity portions 51, 52 of fingers 41, 42, when proximal segments 44, 80, preferably at flats 55, 56 are pivoted toward each other on hinge pin 46, thereby moving the distal portions 43, 45 of fingers 41, 42 away from each other. When the force imposed upon proximal segments 44, 80 of fingers 41, 42 is released, the tension imposed on spring 47 by the closing movement of proximal segments 44, 80, then brings distal extremities 51, 52 into approximation adjacent each other as seen in FIG. 5.

Figure 6:
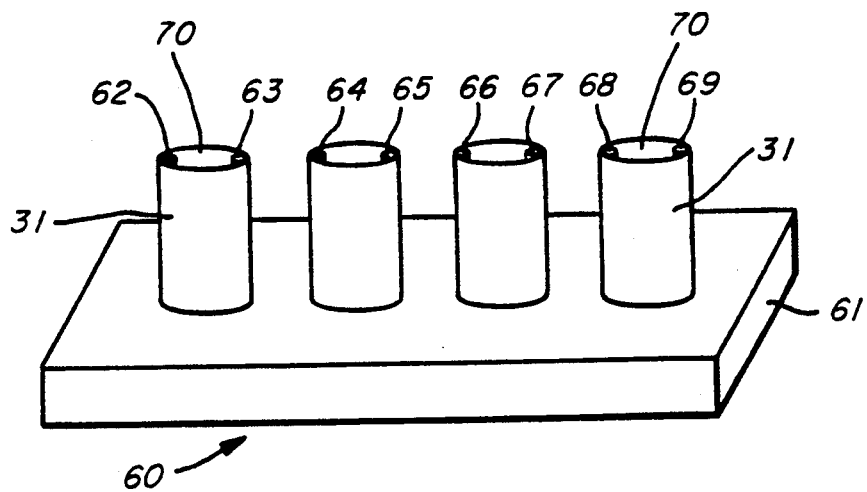
FIG. 6 is an isometric view of a cartridge for holding sheath members for pickup by an applicator, showing the sheath members in place.
Figure 7:
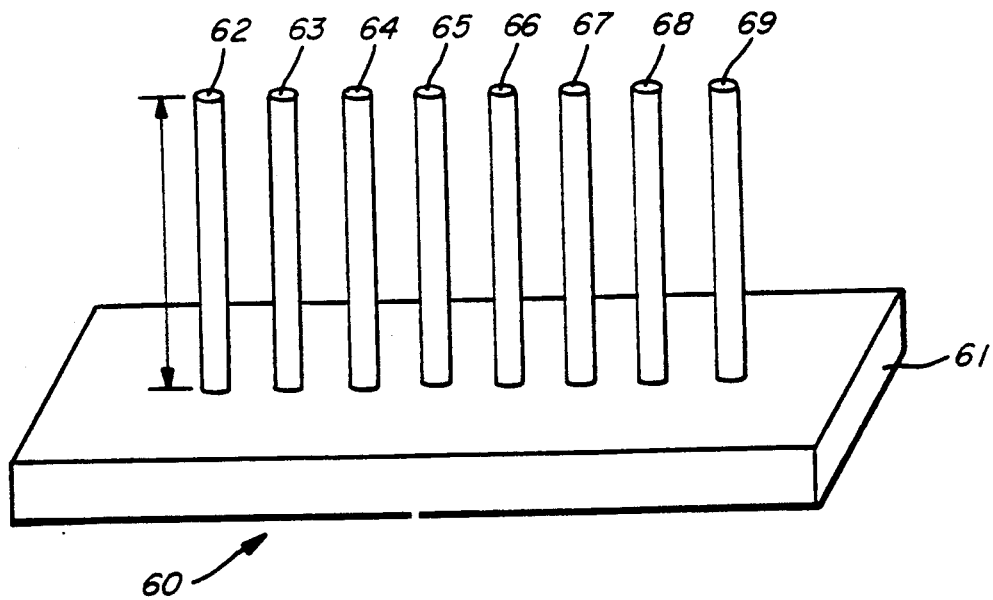
FIG. 7 is an isometric view of the cartridge of FIG. 6, with the sheath members removed.

Referring to FIG. 6, a cartridge 60 for holding sheath members 31 for pickup and loading by applicator 40 includes a base body 61 and a plurality of adjacent pin standards 62-63, 64-65, 66-67, and 68-69, each vertically mounted to base body 61. The pin standards are paired, as at 62-63, at 64-65, at 66-67, and at 68-69. Each pair, for example, 62-63, is spaced apart a distance which will matingly receive a sheath member 31 in tension fit sufficient to secure the sheath member 31 onto the pin pair, as illustrated in FIG. 6. The pin standards 62-69 have lengths at least sufficient to support the sheath members 31 upright when fit onto the pin pairs and preferably have lengths substantially equal to the length of the sheath members 31.

Figure 8:
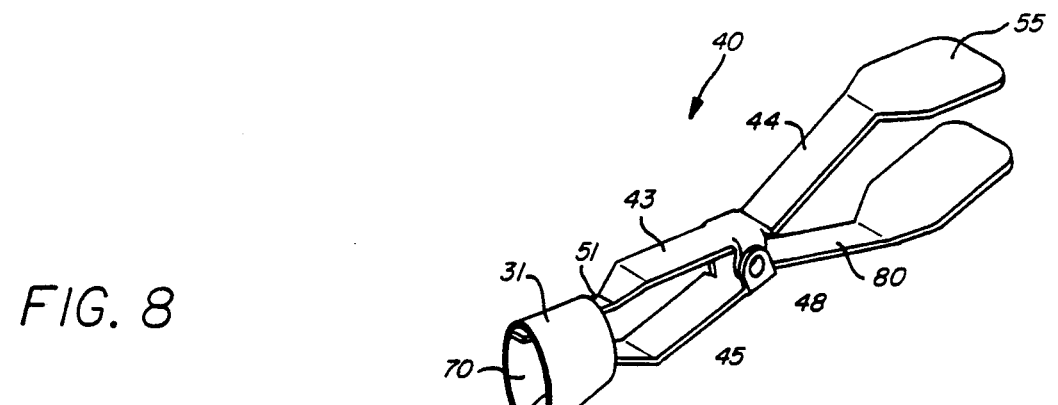
FIG. 8 is an isometric view illustrating the applicator of FIG. 5 holding a sheath member ready for installation on a surgical grasping instrument.
Figure 9:
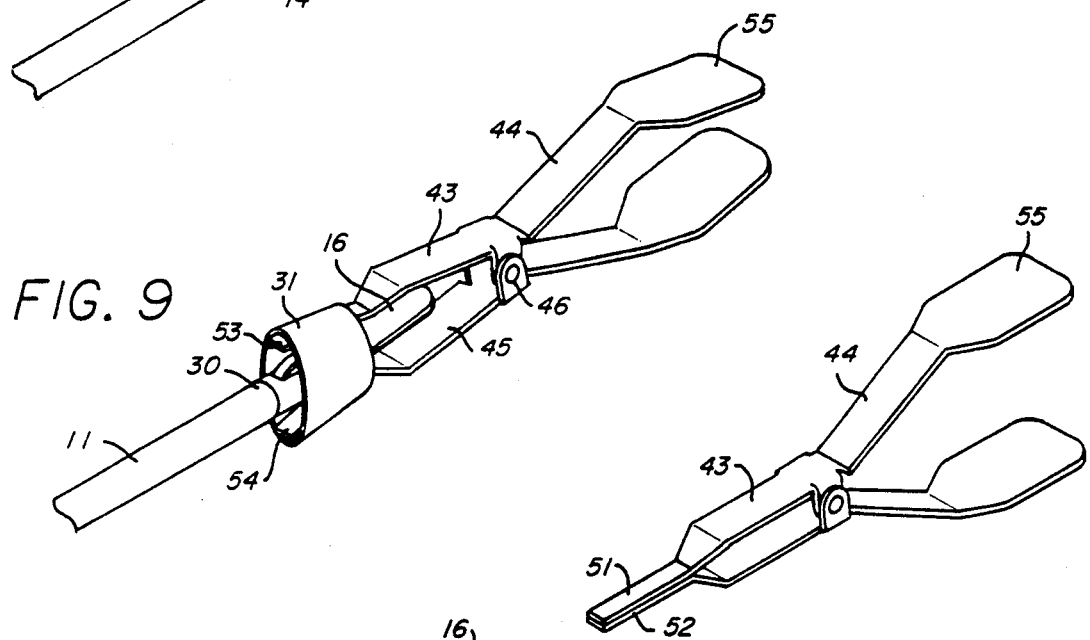
FIG. 9 is an isometric view of the applicator of FIG. 8 and held sheath member, in position for installation of the sheath member on the surgical grasping instrument.

Referring to FIGS. 8-10, the use of applicator 40 to install sheath member 31 onto the proximately unenclosed portion 20, 21 of a grasping member pair 16, 18 of surgical instrument 10 is illustrated. The distal extremity portions 51, 52 of applicator 40 are inserted into the lumen 70 of sheath member 31, which is disposed on, for example, pin standard pairs 62-63 of cartridge 60. The extremity portions 51, 52 of applicator 40 have a length substantially equal to the length of sheath 31. Flats 55, 56 of the proximal portions 44, 80 of applicator 40 are pressed toward each other against the resistance of torsional spring 47, thereby moving the distal segments 43, 45 and their respective distal extremity portions 51, 52 apart from each other to stretch elastic sheath member 31 to a dimension larger than the spacing between pair member 42, 43 and thereby to release sheath member 31 from cartridge 60. Applicator 40 is then withdrawn from cartridge 60 with sheath member 31 disposed on extremity portions 51, 52, as seen in FIG. 8, and is aligned longitudinally with grasping members pair 16, 17 mounted on body 11.

With sheath member 31 expanded by approximation of the proximal portions 55, 56 of applicator 40, applicator 40 is advanced such that the extremity portions 51, 52 advance over tips 18, 19 of grasping members 16, 17, admitting tips 18, 19 between the distal segments 43, 45 of finger members 41, 42 at least until the adjacent distal portion 30 of tubular body 11 is positioned between the ends 53, 54 of the distal segments 43, 45, as shown in FIG. 9. As seen in FIG. 9, the spacing of the hinge pin stands 45-48 from ends 53, 54 of extremity portions 51, 52 is at least the distance between the distal tip 18 of jaw 16 and the adjacent distal portion 30 of body member 11, permitting the advance of the extremity portions 51, 52 of applicator 40 so that ends 53, 54 are adjacent the bridging distal portion of tubular body 11. Pressure on flats 55, 56 is then reduced, permitting the extremity portions 51, 52 to approximate and release sheath 31 to cover the remotely proximal portions 20, 21 of jaws 16, 17 and bridge to adjacent distal portion 30 of body 11, and become fit thereon, so tensioned, as to remain longitudinally in place when the grasping members pair is subsequently actuated, as shown in FIG. 10. The applicator is then withdrawn longitudinally, leaving a surgical grasping assembly which includes the removable elastic sheath member 31 extending over the proximal portion 20, 21 of the grasping member pair 16, 17 bridging to the adjacent portion 30 of the distal segment 13 of body 11.

With sheath 31 in place, the hinge area of the jaws are covered proximally of the operating jaw portion. So covered, entrapment of tissue in the hinge area is prevented. Moreover, when current is applied to jaws 16, 17 for electrocauterizing, the dielectric characteristics of sheath 31 insulate the current from the adjacent anatomy of the patient and focus it on the jaws where electrocauterization is intended, thereby eliminating the risk of inadvertent patient burns in the proximal or hinge portion of the grasping pair.

Having now described our invention, various modifications within the scope of the appended claims will be apparent, and such modifications are intended included within the scope of the claims.

We claim:

1. An applicator system for putting a removable cover or sleeve of a predetermined length onto an instrument, the applicator system comprising:
   spreader means selectively operable to engage the cover or sleeve and expand the cover or sleeve so the cover or sleeve can be received onto the instrument;
   stop means on said spreader means adjacent a distal end thereof to facilitate placement of the cover or sleeve on said spreader means prior to expansion thereof;
   storing means for said cover or sleeve further comprising:
      a base;
      a plurality of rods extending from said base, said rods extending through the cover or sleeve for support thereof until said spreader means is inserted into the cover or sleeve and spread apart for removal of the cover or sleeve from said base and placement on the instrument.

2. The applicator system of claim 1 further comprising:
   an instrument for surgical procedures comprising:
      an elongated body having a proximal and a distal end;
      means for performing a surgical procedure mounted to said distal end of said body, said surgical procedure means actuable between at least two positions, said surgical procedure means growing in transverse cross-section when moving between said positions;
      cover means having a tubular shape when substantially circumscribing and extending longitudinally at least in part over said surgical procedure means and extending toward said distal end of said body, said cover means remaining substantially in place longitudinally while flexing outwardly in response to a force created by said growing in transverse section of said means for performing a surgical procedure, which growing tends apply a force to said cover means tending to pull said cover means in a direction away from said body and said surgical means.

3. The instrument of claim 2, wherein:
   said surgical procedure means comprises a pair of jaws, at least one of which is movable with respect to the other to accomplish an open and closed position;
   said pair of jaws pivotally mounted to each other.

4. The instrument of claim 3, wherein:
   said jaws change in profile adjacent said pivotal mounting as said jaws are moved between said open and closed positions.

5. The instrument of claim 4, wherein:
   said cover means is a sleeve extending over said jaws at the area of said pivotal mounting of said jaws to each other;
   said sleeve having at most a clearance fit over said distal end of said body for retaining said sleeve substantially in a longitudinal position as said jaws are manipulated, causing said sleeve to flex radially.

6. The instrument of claim 5, further comprising:
   actuating means in said body to move said jaws between said open and closed positions.

7. The instrument of claim 6, futher comprising:
   linkage means connecting each of said jaws to said actuating means, said linkage means and jaws assuming no greater profile than said body in said closed position and assuming a greater profile than said body when said jaws are in said open position;
   said sleeve covering said linkage means and said pivotal mounting of said jaws to each other as said jaws are manipulated by said actuating means between said open and closed positions.

8. The instrument of claim 7, wherein:
   said linkage means further comprises:
   two links each having a proximal and distal end pinned to each other and to said actuating means at said proximal ends of said links, one of said links pinned at its said distal end to one of said jaws and the other of said links pinned at its said distal end to the other of said jaws, said pin connections between said jaws and said links both located proximally of said pivotal mounting of said jaws to each other, such that reciprocation of said actuating means causes said jaws to move between said open and closed positions.

9. The instrument of claim 8, wherein said sleeve is made of a polyurethane.

10. The instrument of claim 8, wherein said sleeve is made of rubber.

11. The instrument of claim 8, wherein said sleeve is a dielectric material.

12. The instrument of claim 8, wherein said cover means is a thermoplastic elastomer.

13. The instrument of claim 2, wherein said cover means is made of a polyurethane.

14. The instrument of claim 2, wherein said cover means is made of rubber.

15. The instrument of claim 2, wherein said cover means is made of a dielectric material.

16. The instrument of claim 2, wherein said cover means is a thermoplastic elastomer.

17. The applicator system of claim 1, wherein:
   said stop means further comprises a pair of opposed surfaces actuable away from each other by said spreader means; and
   said stop means further comprises a nonparallel surface extending from each of said opposed surfaces for connection to said spreader means;
   said nonparallel surfaces acting as travel stops for a cover as said pair of opposed surfaces is inserted into a cover for expansion and placement thereof onto an instrument.

18. The applicator system of claim 17, further comprising:
   means for storing covers in a manner to facilitate grasping them with said opposed surfaces.

19. The applicator system of claim 1 further comprising:
   an instrument kit comprising:
      an elongated body having a proximal and a distal end;
      means for performing a surgical procedure mounted to said distal end of said body, said surgical procedure means actuable between an open and closed position, said ssurgical procedure menas growing in transverse cross-section when moving between said open and closed positions;
      cover means having a tubular shape when substantially circumscribing and extending longitudinally at least in part over said surgical procedure means and extending to said distal end of said body, said cover means remaining substantially in place longitudinally while flexing outwardly in response to a force created by said growing transverse cross-section of said means for performing a surgical procedure, which growing tends to apply a force to said cover means tending to pull said cover means in a direction away from said body and said surgical procedure means, said cover means retained to said body and surgical procedure means by virtue of an interference fit thereon resulting from selective operation of said spreader means allowing said cover means to contract onto said body and said surgical procedure means.

20. The instrument kit of claim 19, wherein:
said surgical procedure means comprises a pair of jaws, at least one of which is movable with respect to the other to accomplish said open and closed positions;
said pair of jaws pivotally mounted to each other.

21. The instrument kit of claim 20, wherein:
said jaws change in profile adjacent said pivotal mounting as said jaws are moved between said open and closed positions.

22. The instrument kit of claim 21, wherein:
said cover means is a tubular sleeve extending over said jaws at the area of said pivotal mounting of said jaws to each other;
said sleeve having at most a clearance fit over said distal end of said body for retaining said sleeve in a longitudinal position as said jaws are manipulated, causing said sleeve to flex radially.

23. The instrument kit of claim 19, wherein said cover means is made of a polyurethane.

24. The instrument kit of claim 19, wherein said cover means is made of silicone rubber.

25. The instrument kit of claim 19, wherein said cover means is a dielectric material.

26. The instrument of claim 19, wherein said cover means is a thermoplastic elastomer.

27. The applicator system of claim 1 further comprising:
a removable and disposable sheath, comprising:
an insulating material capable of removable mounting to the body of an instrument to substantially over an assembly mounted to the tip section of the body of the instrument, leaving a selected portion of the instrument exposed for electrocauterization, said insulating material retained against longitudinal movement with respect to the body when subjected to an increase in traverse cross-section of the assembly during its use by virtue of being formed into a tubular shape and interference fitted to the body.

28. The sheath of claim 27, further comprising:
retaining means selectively mountable to said sheath to secure its longitudinal position of the body of the instrument.

29. The sheath of claim 28, wherein:
said insulating material is a sheet formed into a tubular shape and mounted over a portion of the assembly; and
said retaining means encircles said sheet at least in part.

30. The sheath of claim 27, wherein:
said insulating material is preformed into a tubular shape.

31. The sheath of claim 27, wherein said insulating material is a thermoplastic elastomer.

32. The sheath of claim 27, wherein said insulating material is rubber.

33. The sheath of claim 27, wherein said insulating material is polyurethane.

34. An applicator system for putting a removable cover or sleeve of a predetermined length onto an instrument, the applicator system comprising:
spreader means selectively operable to engage the cover or sleeve and expand the cover or sleeve so the cover or sleeve can be received onto the instrument;
stop means on said spreader means adjacent a distal end thereof to facilitate placement of the cover or sleeve on said spreader means prior to expansion thereof;
said stop means further comprises a pair of opposed surfaces actuable away from each other by said spreader means;
said stop means further comprises a nonparallel surface extending from each of said opposed surfaces for connection to said spreader means;
said nonparallel surfaces acting as travel stops for a cover or sleeve as said pair of opposed surfaces is inserted into a cover or sleeve for expansion and placement thereof onto an instrument;
means for storing covers or sleeves in a manner to facilitate grasping them with said opposed surfaces;
said storing means further comprises:
a base;
a plurality of rods extending from said base, said rods extending through the cover or sleeve for support thereof until said opposed surfaces are inserted into the cover or sleeve and spread apart for removal of the cover or sleeve from said storing means and placement on the instrument.

* * * * *